(12) United States Patent
Pei et al.

(10) Patent No.: US 10,231,629 B1
(45) Date of Patent: Mar. 19, 2019

(54) MOBILE INTEGRATED ELECTRODE MULTIFUNCTION SENSOR AND METHOD

(71) Applicant: Maxim Integrated Products, Inc., San Jose, CA (US)

(72) Inventors: Cheng-Wei Pei, Belmont, CA (US); Richard I. Olsen, Truckee, CA (US)

(73) Assignee: MAXIM INTEGRATED PRODUCTS, INC., San Jose, CA (US)

( * ) Notice: Subject to any disclaimer, the term of this patent is extended or adjusted under 35 U.S.C. 154(b) by 481 days.

(21) Appl. No.: 14/799,961

(22) Filed: Jul. 15, 2015

Related U.S. Application Data (60) Provisional application No. 62/041,172, filed on Aug. 25, 2014.

(51) Int. Cl.
*A61B 5/024* (2006.01)
*A61B 5/0408* (2006.01)
*A61B 5/0205* (2006.01)
*A61B 5/00* (2006.01)

(52) U.S. Cl.
CPC .......... *A61B 5/02055* (2013.01); *A61B 5/681* (2013.01); *A61B 5/6898* (2013.01); *A61B 5/7435* (2013.01); *A61B 5/02438* (2013.01); *A61B 5/0408* (2013.01)

(58) Field of Classification Search
CPC . A61B 5/0205; A61B 5/0402; A61B 5/02427; A61B 5/02444; A61B 5/681; A61B 5/0432; A61B 5/0404
See application file for complete search history.

(56) References Cited

U.S. PATENT DOCUMENTS

| 2006/0076236 A1* | 4/2006 | Shah | A61B 5/14532 204/403.01 |
| 2006/0163453 A1* | 7/2006 | Hynes | G01J 1/04 250/214 R |
| 2008/0272446 A1* | 11/2008 | Haluzak | B81C 3/001 257/415 |
| 2009/0105605 A1* | 4/2009 | Abreu | A61B 5/0008 600/549 |
| 2015/0135310 A1* | 5/2015 | Lee | A61B 5/681 726/20 |

* cited by examiner

*Primary Examiner* — Nathan J Jenness
(74) *Attorney, Agent, or Firm* — Kevin E. West; Advent, LLP (57) ABSTRACT

An integrated multifunction sensor, a mobile integrated sensor device, and process are described that include a sensor, where the sensor is used primarily for a first purpose other than as an electrode. In an implementation, an integrated multifunction sensor includes a multifunction sensor configured as a sensor and a first electrode, the multifunction sensor including a lid coupled to a first side of the sensor, where the lid includes a semi-conductive material, and an analog device connected to the lid; where the multifunction sensor is configured to couple to a controller that receives health information from the first electrode and a second electrode. In some embodiments, the integrated multifunction sensor can include an integrated optical sensor. In some implementations, a second electrode may be located elsewhere in a mobile integrated sensor device and complete a differential circuit.

6 Claims, 5 Drawing Sheets

FIG. 2

MOBILE INTEGRATED ELECTRODE MULTIFUNCTION SENSOR AND METHOD

CROSS-REFERENCE TO RELATED APPLICATIONS

The present application claims the benefit under 35 U.S.C. § 119(e) of U.S. Provisional Application Ser. No. 62/041,172, filed Aug. 25, 2014, and titled "ECG ELECTRODE INTEGRATED IN A MULTIFUNCTION PACKAGE LID OF A MOBILE DEVICE SENSOR." U.S. Provisional Application Ser. No. 62/041,172 is herein incorporated by reference in its entirety.

BACKGROUND

Electronic devices, such as smart phones, tablet computers, digital media players, and so forth, increasingly employ sensors to control the manipulation of a variety of functions provided by the device. For example, sensors can be used by electronic devices to detect ambient lighting conditions in order to control the brightness of the device's display screen or detect a fingerprint, etc. Additionally, sensors may be used to detect heat, sound, energy, magnetic fields, etc. Sensors can convert received information into an electrical signal (e.g., a current or voltage).

SUMMARY

An integrated multifunction sensor, a mobile integrated sensor device, and process are described that include a sensor, where the sensor is used primarily for a first purpose other than as an electrode. In an implementation, an integrated multifunction sensor includes a multifunction sensor configured as a sensor and a first electrode, the multifunction sensor including a lid coupled to a first side of the sensor, where the lid includes a semi-conductive material, and an analog device connected to the lid; where the multifunction sensor is configured to couple to a controller that receives health information from the first electrode and a second electrode. In some embodiments, the integrated multifunction sensor can include an integrated optical sensor. In some implementations, a second electrode may be located elsewhere in a mobile integrated sensor device and complete a differential circuit.

In an implementation, a mobile integrated sensor device comprises a mobile device including a multifunction sensor configured as a sensor and an electrode; an amplifier coupled to the multifunction sensor, where the amplifier is configured to detect body electrical potential changes; a controller coupled to the amplifier and the multifunction sensor; and a user interface coupled to the controller.

In an implementation, a process includes initiating a multifunction sensor configured as a sensor and an electrode, where the multifunction sensor is disposed in a mobile device; receiving touch information from the multifunction sensor; using a controller to determine health information using the touch information from the multifunction sensor; and presenting the health information to a user interface.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. The use of the same reference numbers in different instances in the description and the figures may indicate similar or identical items.

DETAILED DESCRIPTION

Overview

Electrocardiography (ECG/EKG) can be used to measure the heart's electrical conduction system. In a typical ECG/EKG circuit, electrodes may be connected to a person and an electronic circuit with patient protection and/or a sensitive amplifier. Some EKG devices may use two electrodes integrated into a mobile device case, not the device itself. Some of these devices can dry electrodes, which include a conductive metal (e.g., platinum, nickel, copper, aluminum, iron, or silver) and conduct a signal from the body through contact only, as opposed to wet electrodes that require a conductive gel to be disposed on the electrodes.

A controller can receive and/or detect subtle electrical potential changes in the body when the heart polarizes and depolarizes and can translate these resulting electrical impulses into a waveform. The waveform can be used to measure the rate and regularity of heartbeats, the size and position of the heart chambers, the presence of damage to the heart, and/or the effects of drugs or devices used to regulate the heart, such as a pacemaker, etc. By measuring electrical signals on the skin in certain locations on the body, it is possible to monitor the health and activity of the heart using these waveforms.

In order for ECG circuits to be integrated into a mobile device, such as a wearable electronic device or a mobile phone, electrodes can be integrated within the device itself. However, space and noise considerations may limit the number and/or location of electrodes that may be incorporated into the device. Challenges in developing sensor devices with an electrode include space considerations integrating an electrode into the end device itself.

Accordingly, an integrated multifunction sensor, a mobile integrated sensor device, and process are described that include a sensor, where the sensor is used primarily for a first purpose other than as an electrode. In an implementation, an integrated multifunction sensor includes a multifunction sensor configured as a sensor and a first electrode, the multifunction sensor including a lid coupled to a first side of the sensor, where the lid includes a semi-conductive material, and an analog device connected to the lid; where the multifunction sensor is configured to couple to a controller that receives health information from the first electrode and a second electrode. In some embodiments, the integrated multifunction sensor can include an integrated optical sensor. In some implementations, a second electrode may be located elsewhere in a mobile integrated sensor device and complete a differential circuit.

In an implementation, a mobile integrated sensor device comprises a mobile device including a multifunction sensor configured as a sensor and an electrode; an amplifier coupled to the multifunction sensor, where the amplifier is configured to detect body electrical potential changes; a controller coupled to the amplifier and the multifunction sensor; and a user interface coupled to the controller.

In an implementation, a process includes initiating a multifunction sensor configured as a sensor and an electrode, where the multifunction sensor is disposed in a mobile device; receiving touch information from the multifunction sensor; using a controller to determine health information using the touch information from the multifunction sensor; and presenting the health information to a user interface.

Example Implementations

FIGS. 1A through 1F illustrate an integrated multifunction sensor 100 and a mobile integrated sensor device 102 in accordance with an example implementation of the present disclosure. As shown in FIGS. 1A through 1F, the integrated multifunction sensor 100 can include an integrated sensor, such as sensor 104, and an integrated electrode, such as electrode 106. Some examples of an integrated multifunction sensor 100 and/or components of an integrated multifunction sensor 100 can include a mobile device, such as a handheld sensor (e.g., a blood pressure cuff, a pulse monitor, etc.), a mobile phone with sensing technology, and/or a wearable, such as a watch, jewelry (e.g., a ring).

In implementations, the sensor 104 can include a temperature sensor, an optical sensor, a gas sensor, an infrared sensor, a pulse sensor, a flash sensor, and/or a proximity sensor. It is contemplated that other types of sensors may be utilized for the integrated sensor 104. In some embodiments, the sensor 104 may include a device input button (e.g., on a smart phone), which can also serve as an electrode 106, or other device. In implementations, electrode 106 can include an electrical conductor used to make contact with a nonmetallic part of a circuit (e.g. a person's finger). In some examples, an electrode 106 can include a silicon or silicon-based portion of the integrated multifunction sensor 100 that can conduct electrical signals. In other examples, the electrode 106 can include metal (e.g., a watch clasp on a wearable smart watch). In implementations, the integrated multifunction sensor 100 is simultaneously a sensor 104 and an electrode 106. For example, the integrated multifunction sensor 100 can be a sensor 104 (e.g., an optical sensor) and simultaneously be an electrode 106 that detects and/or conducts electrical signals when touched by a person's finger.

In some embodiments, the integrated multifunction sensor 100 may include a lid 108, which can be coupled to a side of the integrated multifunction sensor 100. In embodiments, the lid 108 can include materials that are temperature sensing, transmissive, electrically insulating, and/or electrically non-insulating and the lid 108 may be divided into at least two sections. For example, a first section 110 may include a material capable of transmitting visible and near-IR wavelengths (e.g., 400 nm to 1100 nm). In this example, a second section 112 may include a semi-conductive material capable of transmitting IR wavelengths and electrically non-insulating. In other examples, the lid 108 can include glass (e.g., a first section 110) and can include at least one of silicon or germanium (e.g., a second section 112). Silicon and/or germanium may be used for temperature sensing purposes and/or for transmission of mid-IR and long-IR wavelengths (e.g., 1 um to 20 um). In some implementations, the lid 108 may include semiconductor alloys (e.g., gallium arsenide, indium phosphide, arsenic trisulfide, barium fluoride, cadmium sulfide, cadmium telluride, selenium, and so forth). In yet other implementations, the lid 108 may include a metal (e.g., platinum, nickel, copper, aluminum, iron, silver, and so forth). It is contemplated that the lid 106 may include other materials configured to be an electrode and/or a sensor.

Figure 1A:
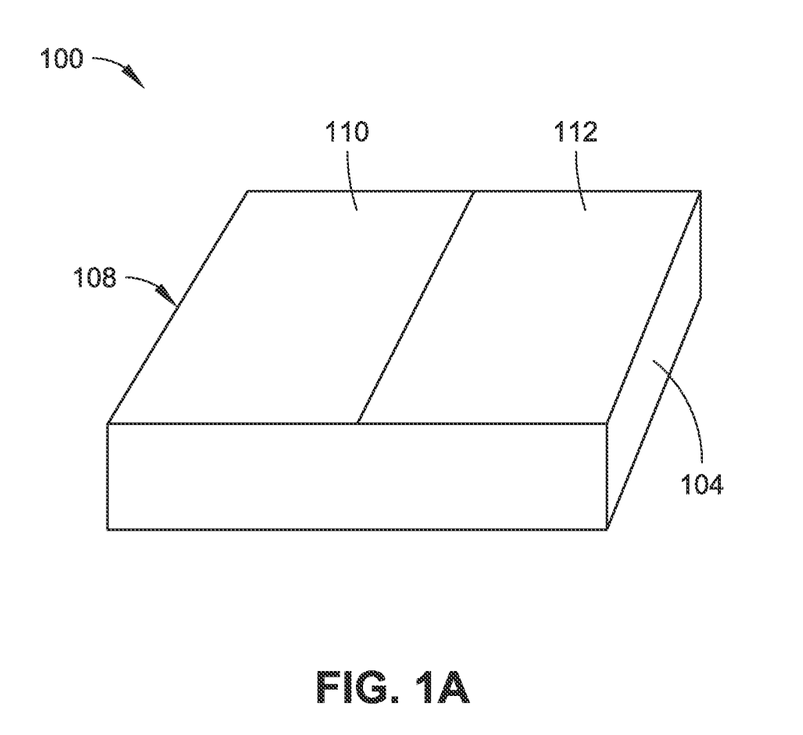
FIG. 1A is an isometric view illustrating an embodiment of an integrated multifunction sensor that integrates a sensor and an electrode within the same device, in accordance with an example implementation of the present disclosure.

In the specific example shown in FIG. 1A, the integrated multifunction sensor 100 includes a sensor 104 with a lid 108, where a first section 110 of the lid 108 is configured for sensing (e.g., a glass section for optical sensing) and a second section 112 (e.g., a silicon and/or germanium section that is an electrode 106) of the lid 108 for conducting an electrical signal (e.g., from a person's finger). In another specific example, the integrated multifunction sensor 100 may not include a lid 108 (e.g., the integrated multifunction sensor 100 may be entirely functional as a sensor 104 and an electrode 106). In this specific example, the integrated multifunction sensor 100 may include a fingerprint sensor, which may also include a pressable input button, where the pressable input button includes a conductive layer (e.g., a thin layer of silicon) configured to receive and/or transmit an electrical signal (e.g., from a finger).

Figure 1B:
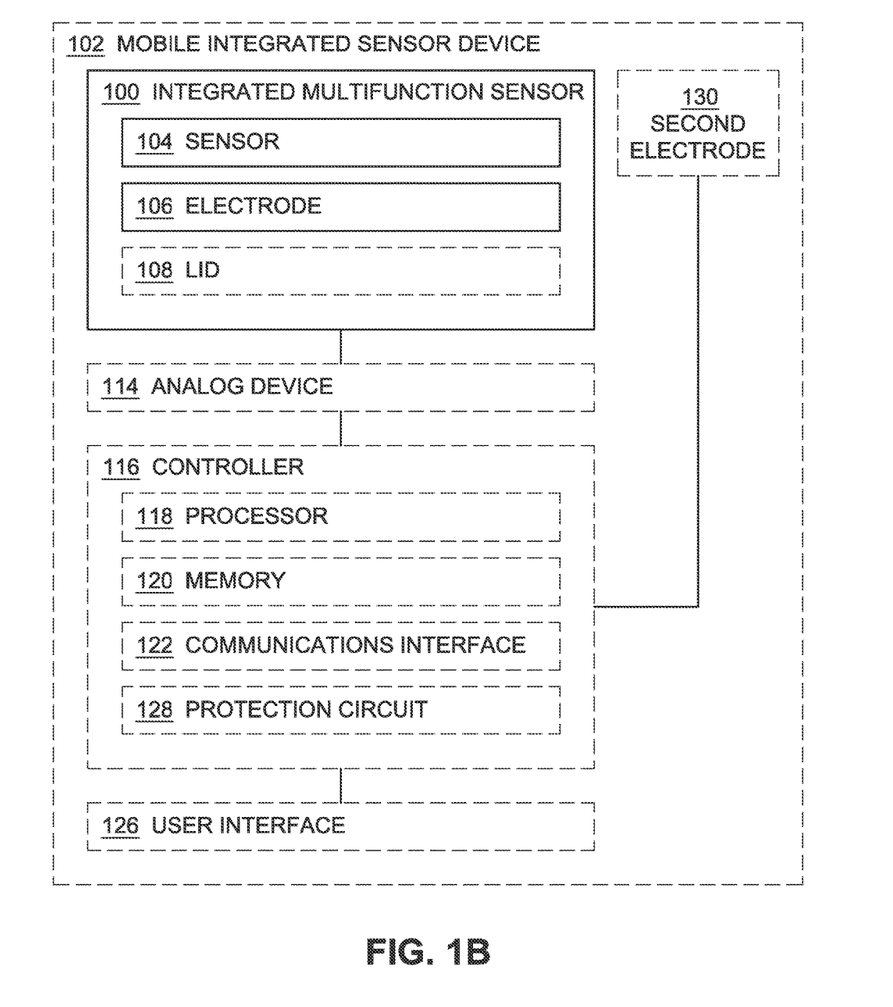
FIG. 1B is an environmental view illustrating an embodiment of a mobile integrated sensor device including an integrated multifunction sensor that integrates a sensor and an electrode within the same device, in accordance with an example implementation of the present disclosure.

As illustrated in FIG. 1B, the mobile integrated sensor device 102 can include a mobile device having an integrated multifunction sensor 100, an analog device 114, a controller 116, a user interface 126, and/or a second electrode 130. In implementations, a mobile device and/or a mobile integrated sensor device 102 may include a small computing device, typically small enough to be handheld having a display screen with touch input and/or a miniature keyboard and weighing less than about two pounds. Some specific examples of a mobile device and/or a mobile integrated sensor device 102 may include a smartphone, a watch (e.g., a smart watch), a computer tablet, etc.

In implementations, the analog device 114 may include an amplifier, which can be used to receive an electrical signal and/or an indication of a body electrical potential change from the integrated multifunction sensor 100 and/or the electrode 106. In such embodiments, the analog device 114 and/or amplifier can be configured to detect subtle changes in electrical potential in the body (e.g. ECG/EKG), which may be used to determine an electrocardiogram waveform. In some implementations, the amplifier 114 may be a portion of the integrated multifunction sensor 100. For example, the amplifier 114 may be disposed within the integrated multifunction sensor 100 and/or coupled to the lid 108 (e.g., electrode 106 and/or semi-conductive section). In other embodiments, the amplifier 114 may be disposed external to the integrated multifunction sensor 100 but internal to the mobile integrated sensor device 102 and coupled to the integrated multifunction sensor 100 and/or a controller 116.

As shown in FIG. 1B, mobile integrated sensor device 102 can include a controller 116 coupled to the integrated multifunction sensor 100, analog device 114, and/or user interface 126 and configured to control and operate the mobile integrated sensor device 102. Referring to FIG. 1B, a mobile integrated sensor device 102, including some or all of its components, can operate under computer control. For example, a processor 118 can be included with or in a mobile integrated sensor device 102 and/or controller 116 to control the components and functions of the mobile integrated sensor device 102 described herein using software, firmware, hardware (e.g., fixed logic circuitry), manual processing, or a combination thereof. The terms "controller," "functionality," "service," and "logic" as used herein generally represent software, firmware, hardware, or a combination of software, firmware, or hardware in conjunction with controlling the mobile integrated sensor device 102. In the case of a software implementation, the module, functionality, or logic represents program code that performs specified tasks when executed on a processor (e.g., central processing unit (CPU) or CPUs). The program code can be stored in one or more computer-readable memory devices (e.g., internal memory and/or one or more tangible media), and so on. The structures, functions, approaches, and techniques described herein can be implemented on a variety of commercial computing platforms having a variety of processors.

As illustrated in FIG. 1B, the controller 116 may include a processor 118, a memory 120, a communications interface 122, and/or a protection circuit 128. A protection circuit 128 can include a circuit configured to protect the mobile integrated sensor device 102 and/or a user from an electrical shock. For example, a protection circuit 128 can include a fuse. The processor 118 provides processing functionality for at least the mobile integrated sensor device 102/controller 116 and can include any number of processors, microcontrollers, or other processing systems, and resident or external memory for storing data and other information accessed or generated by the mobile integrated sensor device 102/controller 116. The processor 118 can execute one or more software programs that implement techniques described herein. The processor 118 is not limited by the materials from which it is formed or the processing mechanisms employed therein and, as such, can be implemented via semiconductor(s) and/or transistors (e.g., using electronic integrated circuit (IC) components), and so forth.

The controller 116 may include a memory 120. The memory 120 can be an example of tangible, computer-readable storage medium that provides storage functionality to store various data associated with operation of the mobile integrated sensor device 102/controller 116, such as software programs and/or code segments, or other data to instruct the processor 118, and possibly other components of the mobile integrated sensor device 102/controller 116, to perform the functionality described herein. Thus, the memory 120 can store data, such as a program of instructions for operating the mobile integrated sensor device 102 (including its components), and so forth. It should be noted that while a single memory 120 is described, a wide variety of types and combinations of memory (e.g., tangible, non-transitory memory) can be employed. The memory 120 can be integral with the processor 118, can comprise stand-alone memory, or can be a combination of both.

Some examples of the memory 120 can include removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, and so forth. In implementations, the mobile integrated sensor device 102 and/or the memory 120 can include removable integrated circuit card (ICC) memory, such as memory provided by a subscriber identity module (SIM) card, a universal subscriber identity module (USIM) card, a universal integrated circuit card (UICC), and so on.

The controller 116 may include a communications interface 122. The communications interface 122 can be operatively configured to communicate with components of the mobile integrated sensor device 102. For example, the communications interface 122 can be configured to transmit data for storage in the mobile integrated sensor device 102, retrieve data from storage in the mobile integrated sensor device 102, and so forth. The communications interface 122 can also be communicatively coupled with the processor 118 to facilitate data transfer between components of the mobile integrated sensor device 102 and the processor 118 (e.g., for communicating inputs to the processor 118 received from a device communicatively coupled with the mobile integrated sensor device 102/controller 116). It should be noted that while the communications interface 122 is described as a component of a mobile integrated sensor device 102/controller 116, one or more components of the communications interface 122 can be implemented as external components communicatively coupled to the mobile integrated sensor device 102 via a wired and/or wireless connection. The mobile integrated sensor device 102 can also include and/or connect to one or more input/output (I/O) devices (e.g., via the communications interface 122), such as a display, a mouse, a touchpad, a touchscreen, a keyboard, and so on.

The communications interface 122 and/or the processor 118 can be configured to communicate with a variety of different networks, such as a wide-area cellular telephone network, such as a 3G cellular network, a 4G cellular network, or a global system for mobile communications (GSM) network; a wireless computer communications network, such as a WiFi network (e.g., a wireless local area network (WLAN) operated using IEEE 802.11 network standards); an internet; the Internet; a wide area network (WAN); a local area network (LAN); a personal area network (PAN) (e.g., a wireless personal area network (WPAN) operated using IEEE 802.15 network standards); a public telephone network; an extranet; an intranet; and so on. However, this list is provided by way of example only and is not meant to limit the present disclosure. Further, the communications interface 122 can be configured to communicate with a single network or multiple networks across different access points. In a specific embodiment, a communications interface 122 can transmit information from the controller 116 to an external device (e.g., a cell phone, a computer connected to a WiFi network, cloud storage, etc.). In another specific embodiment, a communications interface 122 can receive information from an external device (e.g., a cell phone, a computer connected to a WiFi network, cloud storage, etc.).

Generally, any of the functions described herein can be implemented using hardware (e.g., fixed logic circuitry such as integrated circuits), software, firmware, manual processing, or a combination thereof. Thus, the blocks discussed in the above disclosure generally represent hardware (e.g., fixed logic circuitry such as integrated circuits), software, firmware, or a combination thereof. In the instance of a hardware configuration, the various blocks discussed in the above disclosure may be implemented as integrated circuits along with other functionality. Such integrated circuits may include all of the functions of a given block, system, or circuit, or a portion of the functions of the block, system, or circuit. Further, elements of the blocks, systems, or circuits may be implemented across multiple integrated circuits. Such integrated circuits may comprise various integrated circuits, including, but not necessarily limited to: a monolithic integrated circuit, a flip chip integrated circuit, a multichip module integrated circuit, and/or a mixed signal integrated circuit. In the instance of a software implementation, the various blocks discussed in the above disclosure represent executable instructions (e.g., program code) that perform specified tasks when executed on a processor. These executable instructions can be stored in one or more tangible computer readable media. In some such instances, the entire system, block, or circuit may be implemented using its software or firmware equivalent. In other instances, one part of a given system, block, or circuit may be implemented in software or firmware, while other parts are implemented in hardware.

Shown in FIG. 1B, the mobile integrated sensor device 102 can include a user interface 126 coupled to the controller 116. In implementations, a user interface 126 can include an interface between the mobile integrated sensor device 102 and a user. For example, a user interface 126 may include a display, a touchscreen, a touchpad, a switch, a cell phone, and/or a button. It is contemplated that other types of a user interface 126 may be utilized. In specific implementations, the user interface 126 can be coupled to and/or included as a part of communications interface 122. In one specific example, a user interface 126 can include a touchscreen display coupled to a controller 116 and configured for receiving user input and displaying an EKG waveform.

As shown in FIG. 1B, the mobile integrated sensor device 102 may include a second electrode 130. The second electrode 130 can be disposed such that when the integrated multifunction sensor 100 and the second electrode 130 are simultaneously touched by an object, an electrical circuit (e.g., a differential circuit) is formed that can detect an electrical signal from a finger or other object. In some instances, the second electrode 130 may be disposed proximate to the mobile integrated sensor device 102. In other instances, the second electrode 130 may not be disposed proximate to the mobile integrated sensor device 102. In some embodiments, the second electrode 130 can include a conductive or semi-conductive material, such as silicon and/or copper. Additionally, a second electrode 130 can be utilized for common-mode voltage control.

In an implementation, the décor of the sensor 104 is the electrode 106. For example, the décor of the sensor 104, which is and can function as the electrode 106, may include a silicon lid 108, an electrode 106 between at least two lids 108, an electrode 106 proximate to a lid 108, décor proximate to and/or surrounding a sensor 104, décor proximate to and/or surrounding a camera lens 142, a device back panel, glass with an integrated electrode 106 (e.g., a touch panel), and/or a glass electrode.

Figure 1C:
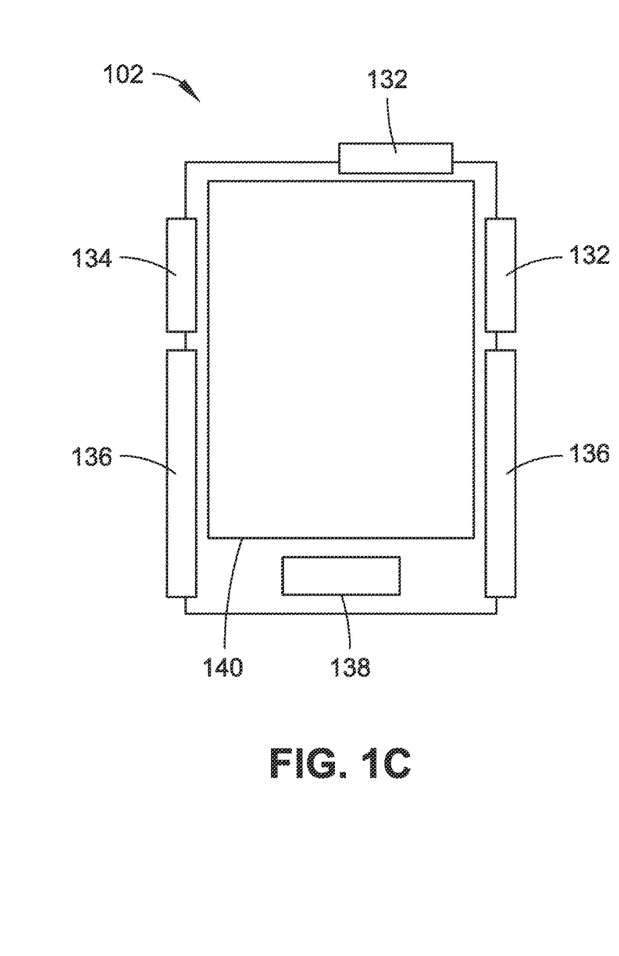
FIG. 1C is a side elevation view illustrating an embodiment of a mobile integrated sensor device including an integrated multifunction sensor that integrates a sensor and an electrode within the same device, in accordance with an example implementation of the present disclosure.
Figure 1D:
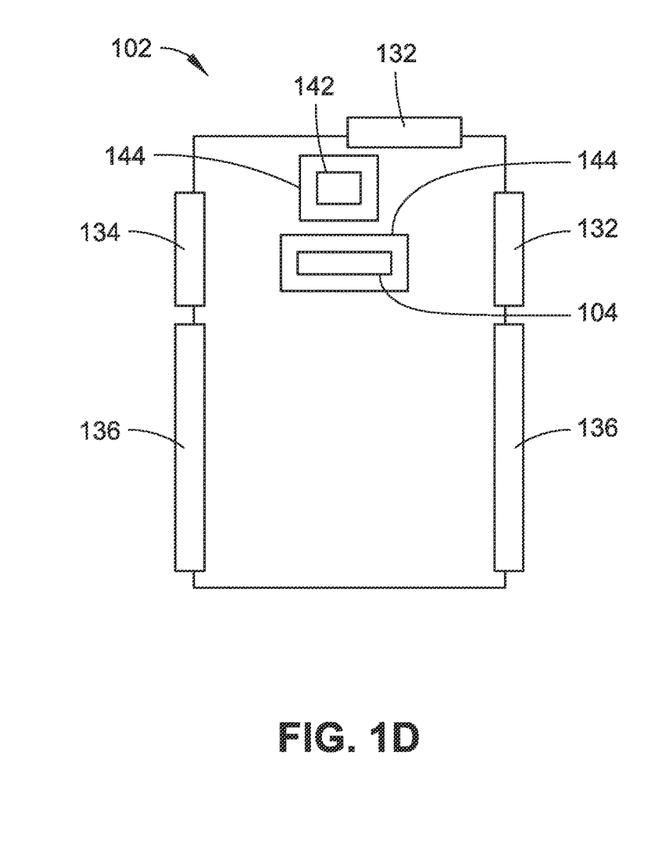
FIG. 1D is a side elevation view illustrating an embodiment of a mobile integrated sensor device including an integrated multifunction sensor that integrates a sensor and an electrode within the same device, in accordance with an example implementation of the present disclosure.

In the specific embodiment illustrated in FIGS. 1C and 1D, a mobile integrated sensor device 102 can include a mobile phone. In this embodiment, at least one component of the mobile phone may serve as the electrode 106. For example, a mechanical button 138 (e.g., a home button, a volume button, a power button 132) can function as an electrode 106, such as a home button electrode. Other examples of an electrode 106 on a mobile integrated sensor device 102 that includes a mobile phone can include side trim 134 and/or an antenna 136 (e.g., an RF antenna 136). Moreover, a mobile phone electrode 106 may include décor proximate to and/or surrounding a camera lens 142 (e.g., a conductive frame 144 that surrounds the camera lens 142). An additional mobile phone example of an electrode 106 can include a sensor 104 and the screen 140 (e.g., glass) of the phone. In this example, the electrode 106 can be disposed in or on the screen 140 as a conductive and/or transparent material. It is contemplated that multiple combinations of a sensor 104 and electrode 106 can be used in a mobile integrated sensor device 102 including a mobile phone.

Figure 1E:
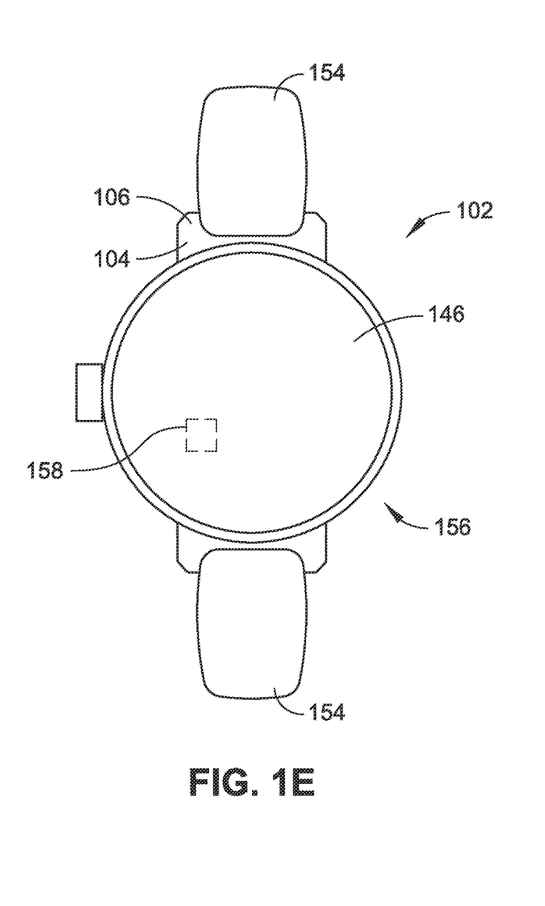
FIG. 1E is a side elevation view illustrating an embodiment of a mobile integrated sensor device including an integrated multifunction sensor that integrates a sensor and an electrode within the same device, in accordance with an example implementation of the present disclosure.
Figure 1F:
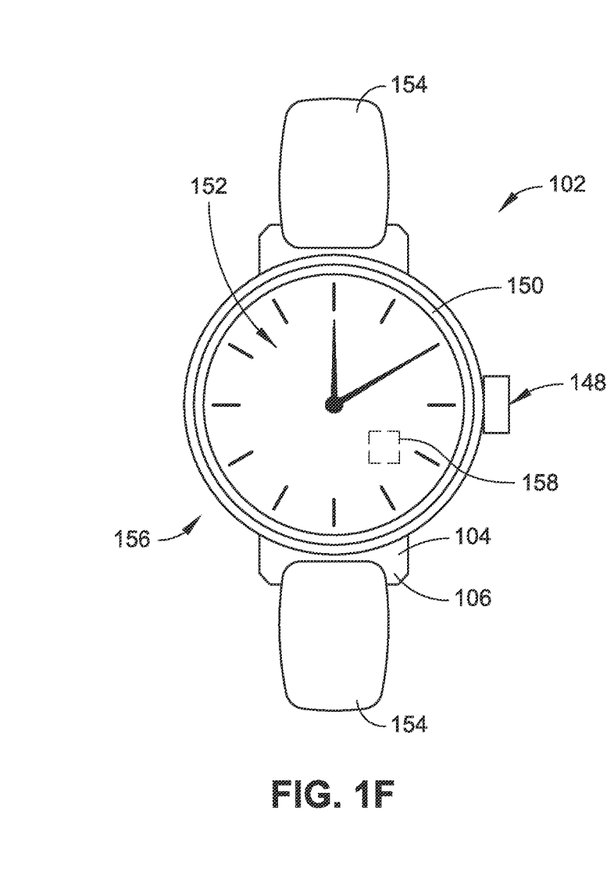
FIG. 1F is a side elevation view illustrating an embodiment of a mobile integrated sensor device including an integrated multifunction sensor that integrates a sensor and an electrode within the same device, in accordance with an example implementation of the present disclosure.

In the specific embodiment illustrated in FIGS. 1E and 1F, a mobile integrated sensor device 102 can include a wearable, such as a watch. In this embodiment, a sensor assembly 158 may be disposed within and/or as a part of the watch. In this embodiment, at least one component of the watch may be an electrode 106. For example, the electrode 106 may include at least a portion of the band 154, a back plate 146, a watch face 152 (e.g., a glass lid or the watch front), a bezel 150, and/or a watch crown 148. For example, the watch may include a band 154 that is an electrode 106 and a watch package 156 that is a sensor 104. In another example, the watch may include a back plate 146 that is a sensor 104 and a watch crown 148 that is an electrode 106. It is contemplated that multiple combinations of a sensor 104 and electrode 106 can be used in a mobile integrated sensor device 102 including a watch.

In additional embodiments, a mobile integrated sensor device 102 can include wireless capability. In implementations, wireless capability may include WiFi, Bluetooth, and/or radio frequency (RF). In one specific embodiment, a mobile integrated sensor device 102 can include a watch with a sensor 104 and/or a sensor assembly 158 and an electrode 106 that includes a jewelry ring with wireless capability that is configured to wirelessly communicate with the sensor 104 and/or the sensor assembly 158. In another specific embodiment, a mobile integrated sensor device 102 can include a mobile phone with a sensor 104 and a watch (or other wearable) having an electrode 106, where the watch and mobile phone have wireless capability that is configured to facilitate wireless communication between the electrode 106 and the sensor 104. In these embodiments, the electrode 106 and/or sensor 104 may be included as a portion of an electrocardiograph (EKG or ECG) system.

Example Processes

Figure 2:
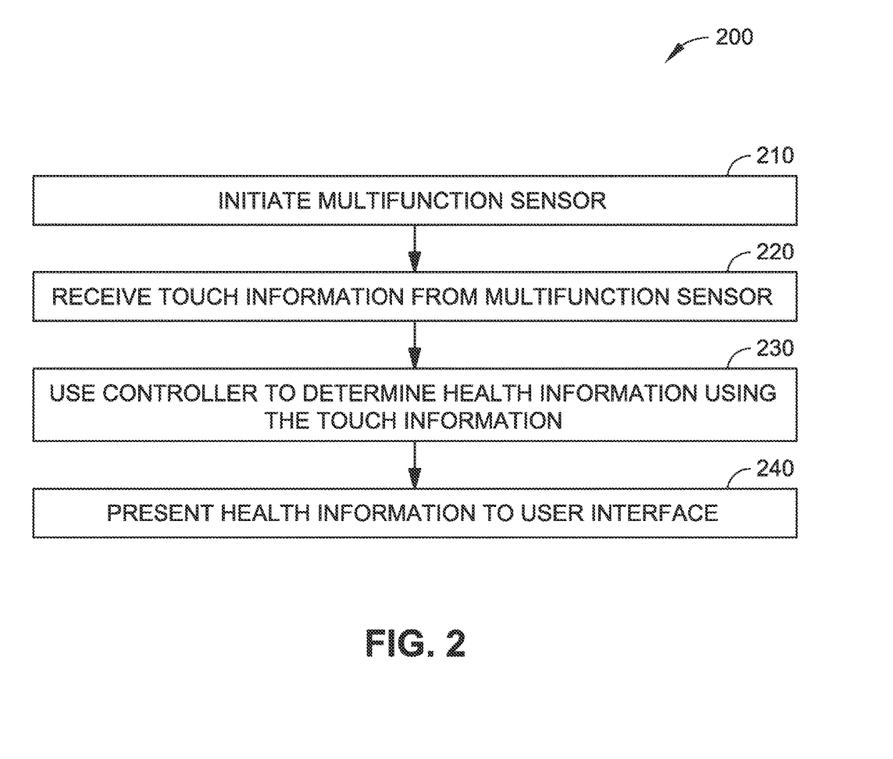
FIG. 2 is a flow diagram illustrating a process in an example implementation for operating a mobile integrated sensor device with an integrated multifunction sensor in accordance with the present disclosure, such as the mobile integrated sensor device and integrated multifunction sensor shown in FIGS. 1A through 1F.

The following discussion describes example techniques for operating a mobile integrated sensor device, such as the integrated multifunction sensor 100 and/or the mobile integrated sensor device 102 shown in FIGS. 1A through 1F. FIG. 2 illustrates an example process 200 for operating the integrated multifunction sensor 100 and/or the mobile integrated sensor device 102 shown in FIGS. 1A through 1F.

In the process 200 illustrated in FIG. 2, an integrated multifunction sensor is initiated (Block 210). In embodiments, initiating an integrated multifunction sensor 100 can include using a controller 116 to transmit a signal to the integrated multifunction sensor 100 to begin operation (e.g., begin sensing, begin detecting an indication of a touch event, begin detecting an electrical signal, etc.). In one specific example, initiating the integrated multifunction sensor 100 can include initiating controller 116 to receive an indication of a detected electrical signal from integrated multifunction sensor 100 and/or the electrode portion (e.g., electrode 106) of the integrated multifunction sensor 100.

Touch information is then received from the integrated multifunction sensor (Block 220). In embodiments, receiving touch information from the integrated multifunction sensor 100 can include using controller 116 to receive at least one electrical signal from the integrated multifunction sensor 100 and/or electrode 106. Some examples of touch information can include an indication of a positive touch event and/or an electrical signal from a finger (e.g., a change in body electrical potential change). It is contemplated that other types of information can be received by controller 116 from integrated multifunction sensor 100 (e.g., information from the sensor portion of the integrated multifunction sensor 100, such as an indication of a fingerprint from a fingerprint sensor, an indication of a proximate object from a proximity sensor, etc.). In some embodiments, touch and/or other information may be received from an analog device 114, such as an amplifier, which can be configured to detect changes in electrical potential in a finger or person's body (e.g., ECG/EKG).

Then, a controller is used to determine health information using received touch information (Block 230). In embodiments, using a controller 116 to determine health information can include using a controller 116 to determine an ECG/EKG waveform using touch information, such as electrical signals received from a user's finger and/or body. Examples of health information can include an ECG/EKG waveform, an indication of heart activity, etc. Additionally, controller 116 can determine health information such as heartbeat information, heart characteristics, and/or heart damage.

Next, health information is presented by controller to a user interface (Block 240). In implementations, presenting health information to a user interface 126 can include using a controller 116 to present health information, such as an ECG/EKG to a user interface 126, such as a touchscreen display. In implementations, the user interface 126 can further present the health information to a user.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. An integrated multifunction sensor, comprising:
   an optical sensor;
   a lid wherein a first section of the lid comprises a material operable to transmit visible and near infra-red (IR) wavelengths and a second section of the lid comprises a semi-conductive material operable to transmit IR wavelengths and further operable to conduct electrical signals when contacted by a person's body;
   a first electrode operable to detect electrical signals when the lid is contacted by a person's body;
   an analog device connected to the lid, the analog device comprising an amplifier configured to detect changes in electrical potential when the lid is contacted by the person's body;
   a second electrode operable to complete a differential circuit when the lid and the second electrode are simultaneously contacted by the person's body; and
   a controller operable to receive information from the optical sensor, the first electrode, the analog device and the second electrode and output health information about a user.

2. The integrated multifunction sensor as recited in claim 1, further comprising at least one of: a temperature sensor, a gas sensor, an infrared sensor, a pulse sensor, a flash sensor, an EKG sensor, or a proximity sensor.

3. The integrated multifunction sensor as recited in claim 1, wherein the lid includes at least one of silicon or germanium.

4. The integrated multifunction sensor as recited in claim 1, wherein the analog device receives an indication of changes in electrical potential in a person's body.

5. The integrated multifunction sensor as recited in claim 1, wherein the controller is configured to determine an electrocardiogram using body electrical potential changes detected by the multifunction sensor.

6. The integrated multifunction sensor as recited in claim 1, wherein the integrated multifunction sensor is configured for use in at least one of a wearable, a mobile phone, or a watch.

* * * * *